(12) United States Patent  
Gill

(10) Patent No.: US 6,306,076 B1
(45) Date of Patent: Oct. 23, 2001

(54) MAGNOTHERAPY DEVICE WHICH CAN BE ATTACHED TO A HUMAN OR ANIMAL

(76) Inventor: Richard Austin Gill, 11 Sage Close, Beverley East Yorkshire (GB), HU17 8WH ( * ) Notice: Subject to any disclaimer, the term of this patent is extended or adjusted under 35 U.S.C. 154(b) by 0 days.

(21) Appl. No.: 09/313,629

(22) Filed: May 18, 1999

(30) Foreign Application Priority Data

Sep. 23, 1997 (GB) .................................................. 2320435

(51) Int. Cl.$^7$ .............................. A61N 2/08; A61N 2/12; A61G 15/00
(52) U.S. Cl. ............................................................. 600/15
(58) Field of Search ............................................. 600/9–15

(56) References Cited

U.S. PATENT DOCUMENTS

| | | | |
|---|---|---|---|
| 4,727,857 | * | 3/1988 | Horl ......................................... 600/9 |
| 5,295,494 | * | 3/1994 | Rodriguez ................................. 600/9 |
| 5,304,111 | * | 4/1994 | Mitsuno et al. .......................... 600/9 |
| 5,323,499 | * | 6/1994 | Chan ........................................ 600/9 |

FOREIGN PATENT DOCUMENTS

| | | | |
|---|---|---|---|
| 3726364 | * | 2/1989 | (DE) ........................................ 600/9 |
| 2112645 | * | 7/1983 | (GB) ........................................ 600/9 |

\* cited by examiner

*Primary Examiner*—Samuel G. Gilbert

(57) ABSTRACT

A device for treating human beings or animals, e.g. horses, may be attached to a strap and has a first disc-shaped magnet (1) rotatably mounted on pins (6) within a second annular magnet (3), and held in place by a plate (8). The upper surface of the second magnet (3) is a south pole and the lower surface is a north pole. The first magnet can be rotated through 180 degrees so that its top surface can be chosen to be a north or south pole. The whole device can be removed from its strap and inverted so that different poles can be adjacent the skin in use. A uniform magnetic field of either polarity, or an alternating field can thus be applied to the wearer.

20 Claims, 9 Drawing Sheets

MAGNOTHERAPY DEVICE WHICH CAN BE ATTACHED TO A HUMAN OR ANIMAL

CROSS-REFERENCE TO RELATED APPLICATIONS

International Application Published under the Patent cooperation Treaty (PCT), International Patent Classification A61N 2/06, International Publication Number W0 99/15233, International Publication Date Apr. 1, 1999, International Application Number PCT/GB98/02855, International Filing date Sep. 21, 1998, Priority Date 9720108.1 Sep. 23, 1997.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

It has been found that by causing a magnetic flux to act on a human body, certain conditions such as arthritis, ligament and tendon strains, and muscle stiffness can be alleviated.

A device comprising a bandage having a plurality of magnets therein is described in GB 2 168 898. The bandage is wrapped around a part of the body so that magnetic flux passes therethrough, thereby increasing blood flow in that part of the body. Adjacent magnets within the bandage are arranged so that the poles alternate, i.e. a north pole has south poles to either side of it. Empirical evidence shows that, in certain conditions, the benefit of such an arrangement of poles is greater than the case where adjacent magnets have the same poles facing in the same direction.

A magnotherapy device to be worn around the wrist is described in GB 2 307 178. In this device one magnet and an oversized plate are arranged so that blood flowing beneath the magnet and the plate is subjected to two changes in polarity.

Empirical evidence demonstrates that magnotherapy has beneficial effects. Where the problems arises from general poor circulation, i.e. shortage of blood and therefore oxygen to particular tissue, a diffuse magnetic field would appear to be required. Where muscular pain through strain is to be treated it would appear that a concentrated field directed to the affected area would be most beneficial. Where the problem is associated with crystalline deposits in joints it is thought that by directing a concentrated magnetic field towards the deposit the crystal will be distorted thereby easing natural removal. This latter technique is believed to reduce or eliminate the build up of intransigent scale.

It has been found that for the same ailment on different people, one arrangement of magnets may provide a beneficial result on one person, whilst on another person a different arrangement of magnets may be required to provide the same result. Even on the same person, different ailments may require different arrangements of magnets to provide beneficial results.

It would therefore be desirable to provide a simple magnotherapy device which is not restricted in the same way that presently available devices are.

BRIEF SUMMARY OF THE INVENTION

The invention provides a magnotherapy device comprising at least two magnet members mounted by mounting means, wherein each magnet member has opposing north and south poles, and at least one of the magnet members is mounted so as to be movable relative to another of the said magnet members, thereby enabling the poles of any two adjacent magnet members facing in the same direction to be either opposite or identical.

The said at least one of the magnet members which is mounted so as to be movable relative to another of the said magnet members may be rotatably mounted.

Preferably, the mounting means is a housing.

An outer magnet member may be mounted in the housing, and an inner magnet member may be mounted within the outer magnet member. Preferably, the inner magnet member is rotatably mounted within the outer magnet member. Advantageously, means to maintain the inner magnet member in a fixed position relative to the outer magnet member are provided. The said means may comprise at least one co-operating indent and protrusion, one being mounted on the outer magnet member, and the other being mounted on the inner magnet member. Preferably, the protrusion is formed from a resilient material. Alternatively or additionally, the means to maintain the inner magnet member in a fixed position relative to the outer magnet member may comprise a plate. The plate may be releasably attachable to the said housing. Advantageously, the plate is formed from steel. The plate may be movably mounted on the housing. The plate may be mounted on either side of the said housing. The plate and housing may be so shaped and dimensioned as to permit sliding of the plate on the housing.

In one embodiment of the invention, the outer magnet member, and/or the inner magnet member comprises a magnet mounted in a casing, and preferably the casing is formed from two halves, which may interlock. More preferably, the casing of the outer magnet member is the housing.

The magnotherapy device may comprise a strap to permit attachment of the device to a part of the body, for example the wrist. The strap may be adjustable.

Preferably, the device comprises at least one plug having at one end thereof a means for attachment to a strap, and at the other end thereof means for attachment to the said housing. The means for attachment to the said housing may comprise a resiliently mounted member having a protrusion thereon for engagement with an indent in the said housing. More preferably, the device comprises two of the said plugs, each being engagable with the said housing.

In a preferred embodiment of the invention, the inner magnet member is in the form of a disc. The outer magnet member suitably has a space therein in which the inner magnet is mounted. Preferably, the space is an aperture. The outer magnet member may be substantially circular.

Advantageously, at least one of the magnets is a neodymium magnet.

The magnetic field strength provided by the inner magnet is preferably at least 200 gauss at a distance of 10 mm from the housing.

In one embodiment of the invention, means for rotating the rotatably mounted magnet member is provided.

By providing a magnet member which is movable relative to another magnet member, it is possible to provide for an alternating magnetic field i.e. north, south, north or a continuous magnetic field, i.e. north, north, north. By rotating the housing, further configurations are possible, i.e. south, north, south, or south, south, south.

Both poles of the magnet relieve pain, but it has been found that the north pole is particularly effective in relieving conditions such as infection or inflammation, whereas the south pole is particularly effective for conditions causing stiffness such as poor blood circulation. Furthermore, since inflammation or infection often precedes poor blood circulation, it is useful to be able to treat a region with a south pole after treatment with a north pole.

The invention also provides a method of treating a human or animal comprising the step of fastening a magnotherapy device according to the invention to the said human or animal.

The device of the invention may be used on humans or animals, in particular horses.

BRIEF DESCRIPTION OF THE SEVERAL VIEWS OF THE DRAWINGS

In the drawings, which illustrate an exemplary embodiment of the invention:

FIG. 8a is a plan view of the magnetic field shown in FIG. 7a; and

DETAILED DESCRIPTION OF THE INVENTION

Figure 2:
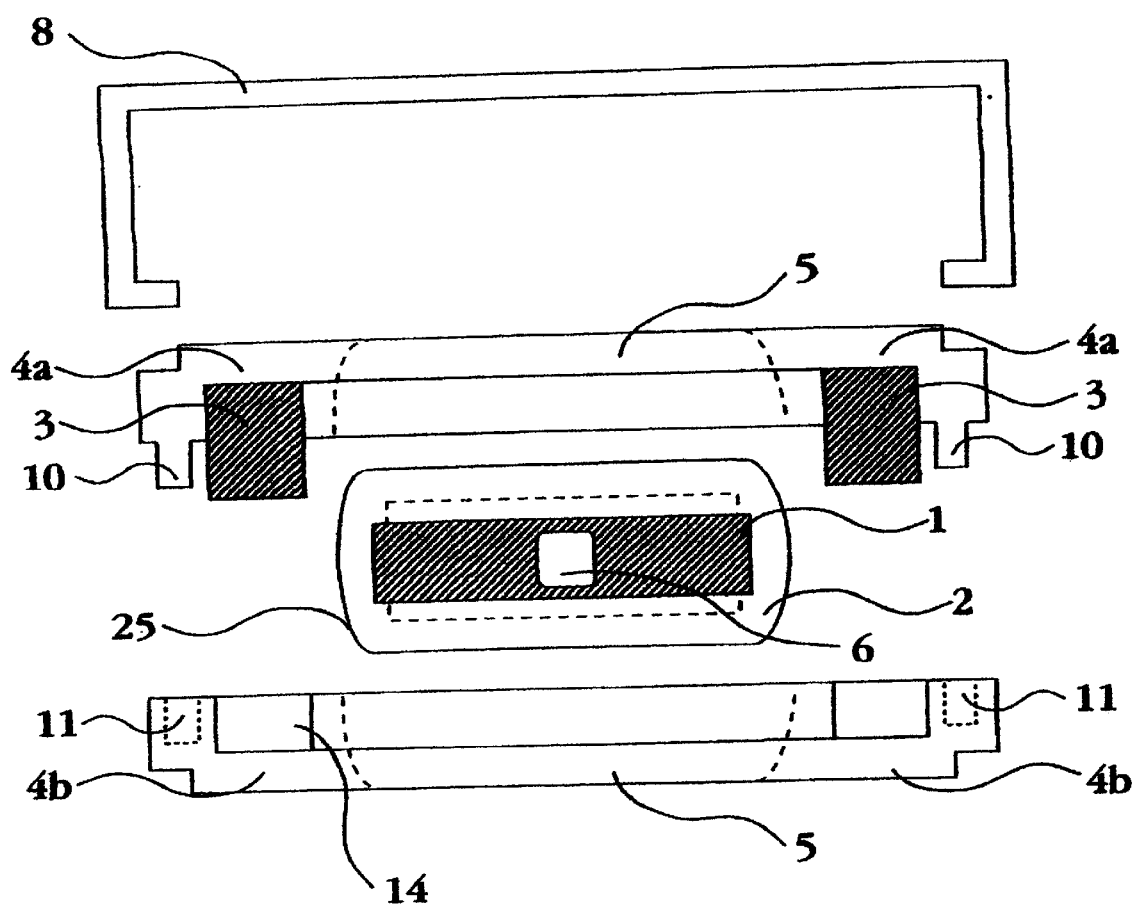
FIG. 2 is an exploded end view of a magnotherapy device according to the invention.
Figure 3:
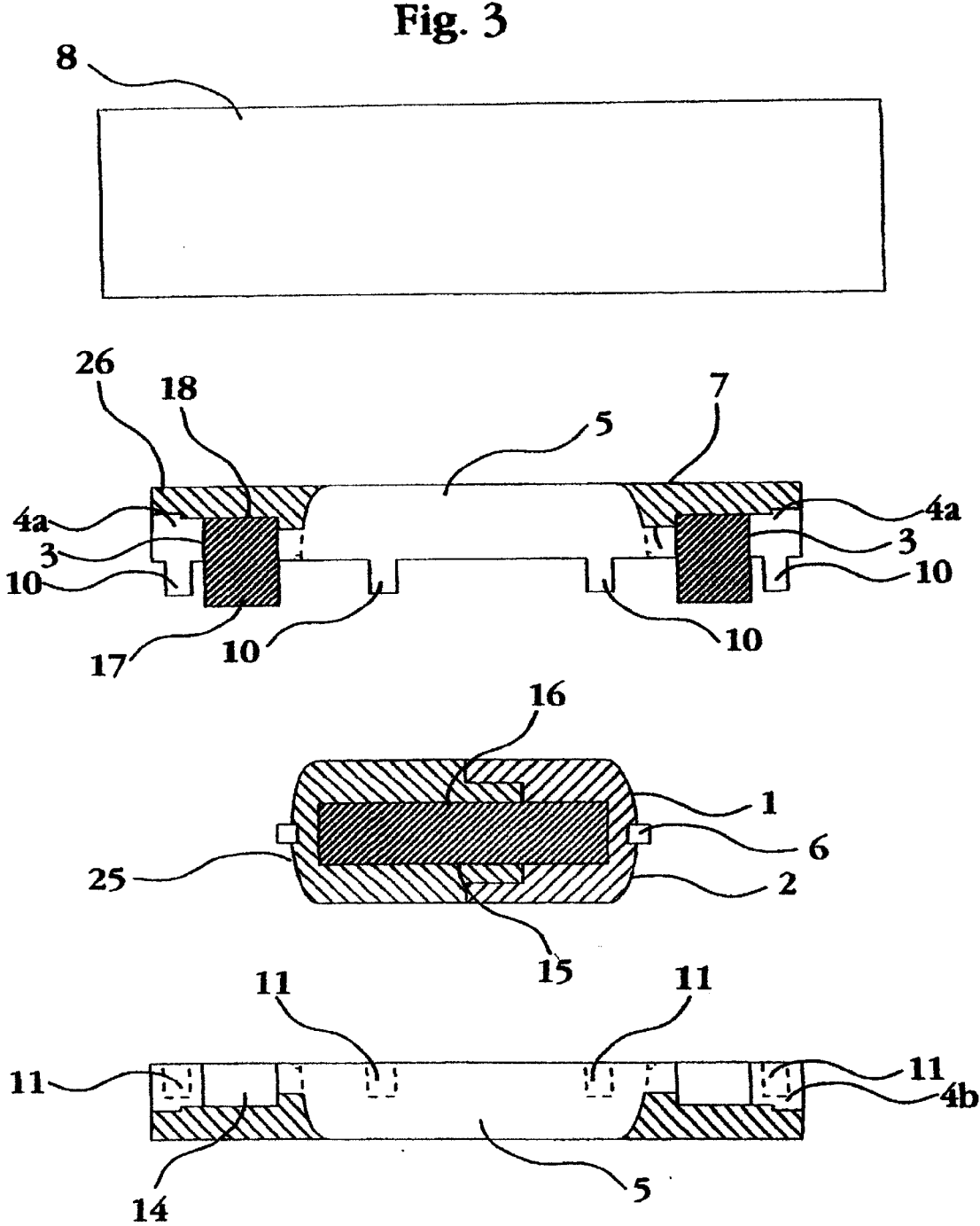
FIG. 3 is a cross section of the device shown in FIG. 2.
Figure 4:
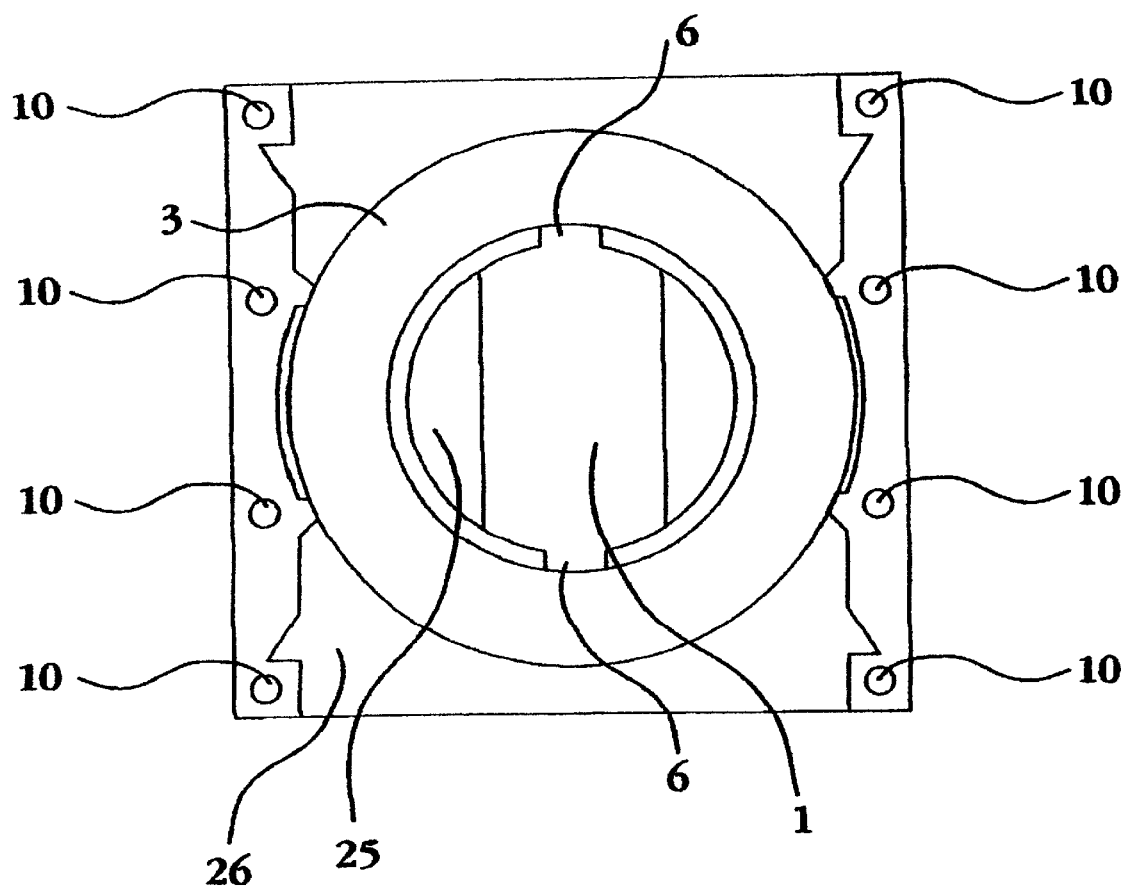
FIG. 4 is a plan view of the device shown in FIG. 2.
Figure 5:
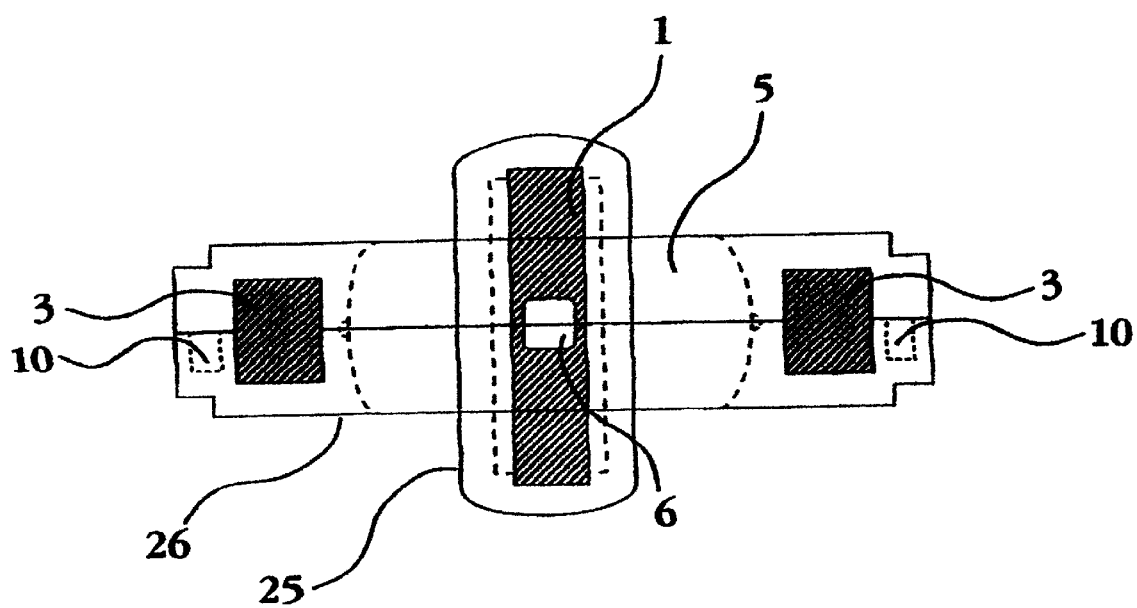
FIG. 5 is an end view of an assembled magnotherapy device as shown in FIG. 2, where the inner magnet is rotated through 90 degrees.

FIGS. 2 and 3 illustrate an inner magnet member 25 comprising a magnet 1 mounted in a casing 2. Casing 2 is formed from two halves which are a push fit, the magnet 1 being encased therein. Around the circumference of the casing 2 there are mounted protrusions 6. Protrusions 6 are in the form of pins which are rotatably mounted in an outer magnet member 26 and provide for rotation of the inner magnet member 25 with respect to the outer magnet member 26. The plate 8 shown in FIG. 3 has been rotated through 90 degrees from the position shown in FIG. 2.

Outer magnet member 26 comprises a magnet 3 mounted in a casing, the said casing comprising an upper half 4a and a lower half 4b. The lower half 4b is provided with a plurality of holes 11, each so dimensioned as to receive as a push fit, a pin 10 of the upper half 4a. In the embodiments shown, eight pins 10 and bores 11 are provided. Both the upper half 4a and the lower half 4b are provided with a circular recess 14 in which the outer magnet 3 sits. The backing plate 8 slides onto the assembled casing and ensures the inner magnet member 25 stays in the desired position.

The cut away portions 5 of the upper half 4a and lower half 4b are so shaped as to provide sufficient a gap between the outer casing 2 of the inner magnet member 25 and the inner circumferential edge of the casing halves 4a, 4b so as to enable the inner magnet member 25 to be rotated through 360 degrees.

Referring again to FIG. 3, the upper surface 16 of inner magnet 1, and hence inner magnet member 25, is a north pole, whereas the lower surface 15 is a south pole. The upper surface 18 of outer magnet member 3, and hence outer magnet member 26, is a south pole, whereas the lower surface 17 is a north pole. This means that when the device is worn in the manner shown in FIG. 1, the wearer will be subjected to an alternating magnetic field insofar as the flood flowing beneath the device will first experience a north pole followed by a south pole, followed by another north pole. If the whole device is turned over and the steel backing plate is removed and refitted to the other side of the casing, the wearer will be subjected to a south, north, south changing polarity. Alternatively, a continuous magnetic field may better suit the wearer, in which case the inner magnet may be rotated so that one surface of the device provides a north pole whilst the other surface provides a south pole. The device is simply turned over and the steel backing plate reversed to present the correct face to the wearer's skin.

Figure 6:
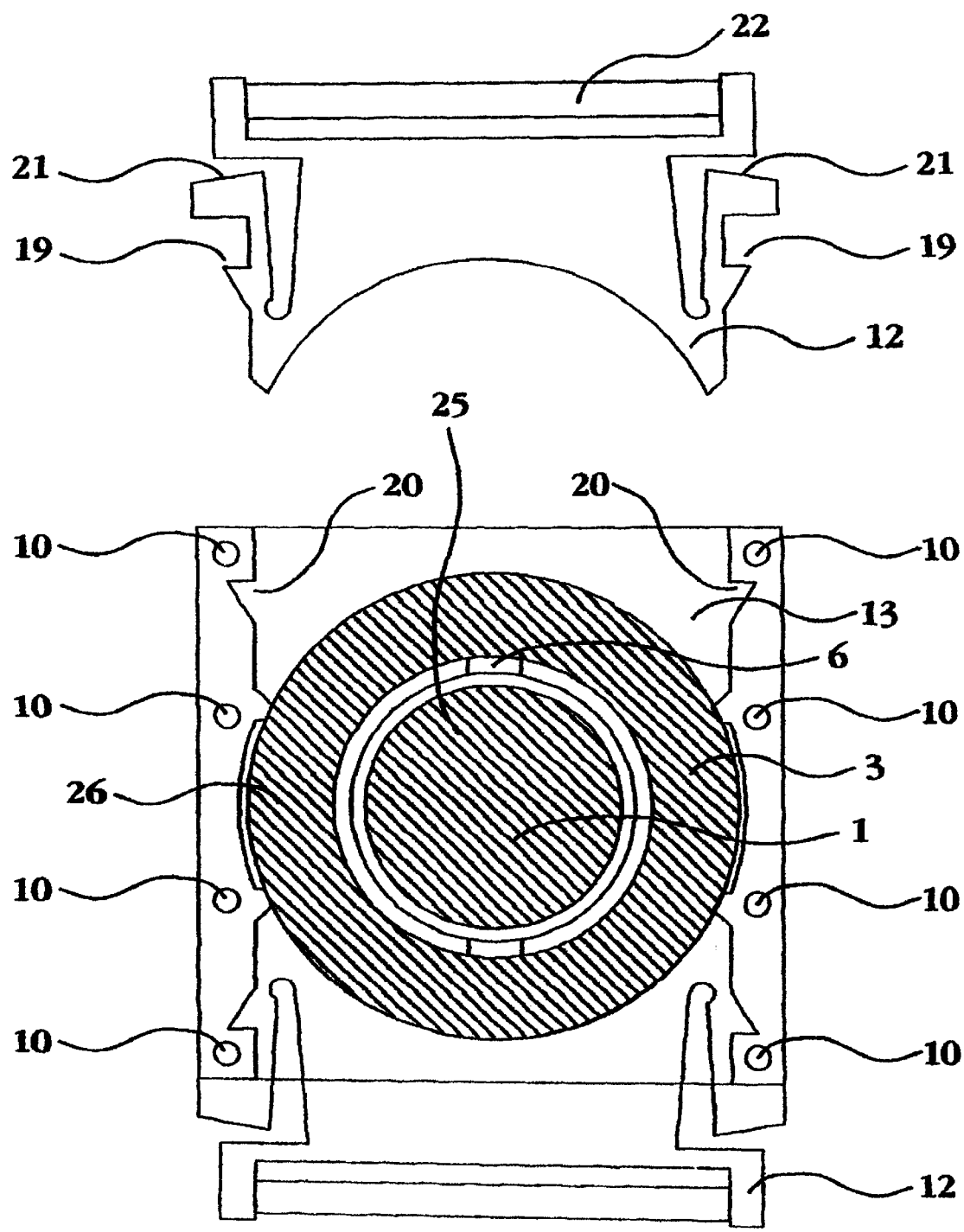
FIG. 6 is a plan view of a magnotherapy device without a backing plate having fittings for attachment to a strap.

Referring now to FIG. 6, a plug 12 for attachment to the magnotherapy device is provided, the said plug 12 having at one end thereof a pin 22 suitable for attachment to a wrist strap. The wrist strap is not shown since such straps are well known to those skilled in the art. Similarly, pin 22 is not described in detail. To each side of the plug 12 there is provided a sprung member having a protrusion 19 which engages with indent 20 in the casing of the outer magnet member 26, so that when the plug 12 is pushed into the casing it is retained therein. When it is desired to release the plug 12 from the casing, portions 21 are pressed inwardly until protrusion 19 is clear of indent 20, thereby allowing the plug to be withdrawn from the casing. The magnotherapy device can then be rotated through 180 degrees and the plugs 12 refitted thereto to provide for a different combination of magnetic poles to face the wearer's skin. Alternatively, it may be desired to use the same strap with magnets of different strength.

Figure 1A:
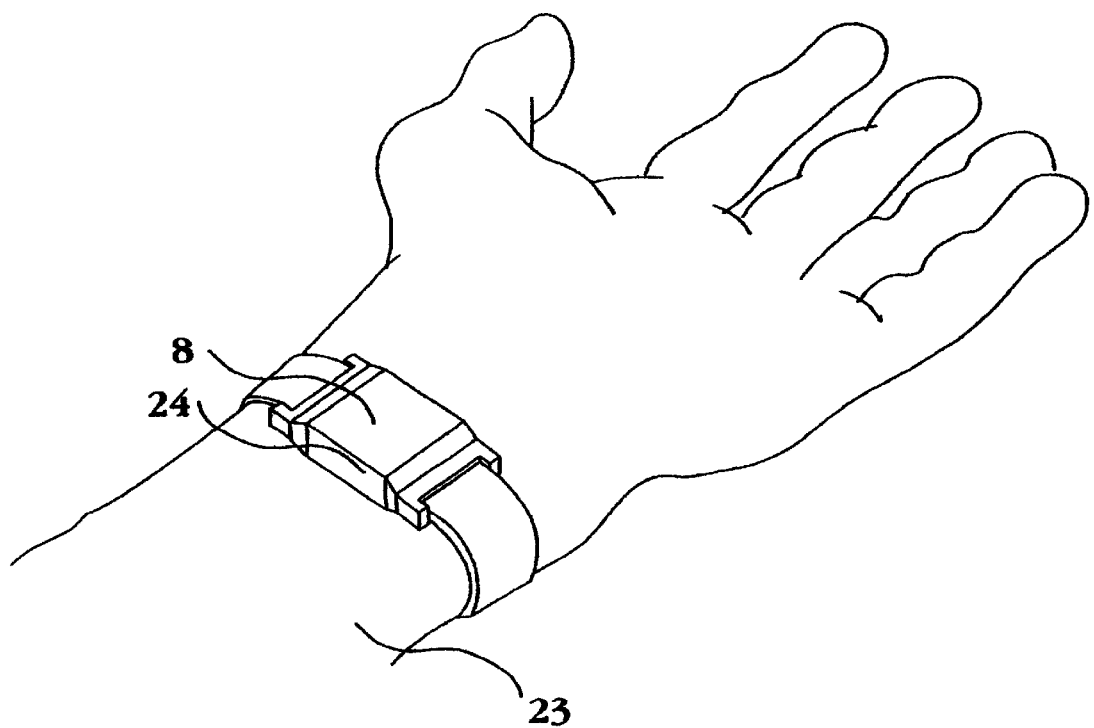
FIG. 1a is a schematic representation of a user wearing a magnotherapy device according to the invention; with a backing plate in place.

FIG. 1a shows a magnotherapy device 24 attached by means for a strap to a wearer's wrist 23, the device having a backing plate 8 mounted thereto.

Figure 1B:
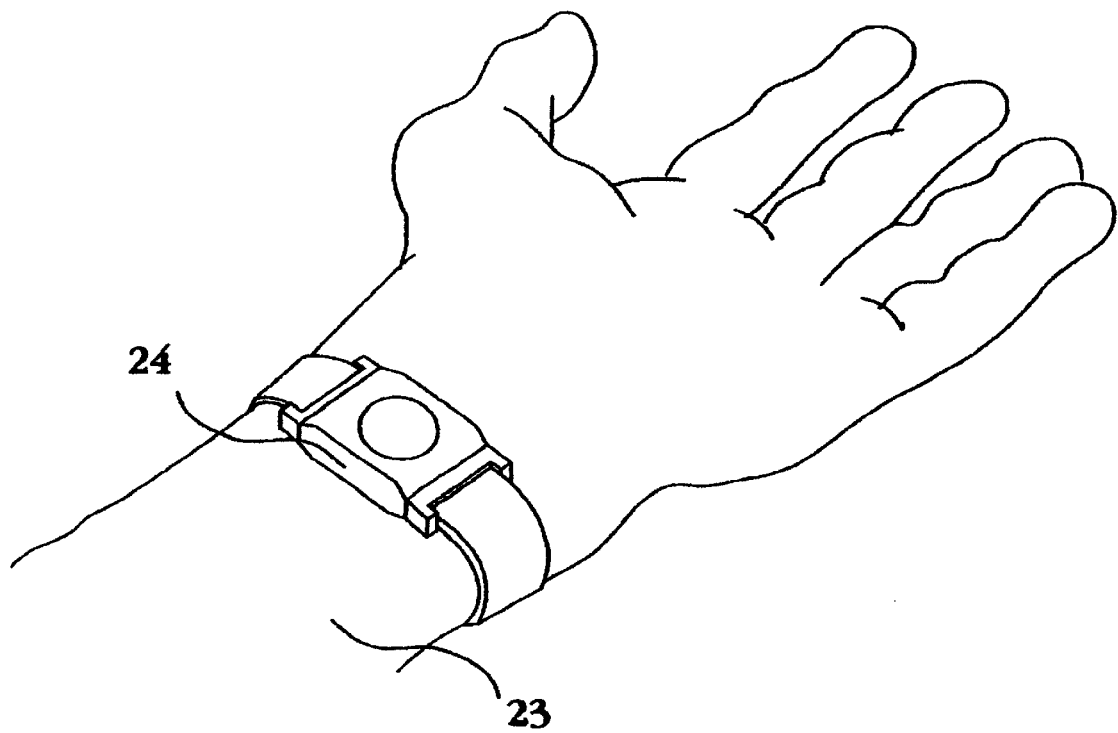
FIG. 1b is a schematic representation of the device shown in FIG. 1a, without a backing plate.

FIG. 1b shows a magnotherapy device 24 according to the invention attached to a wearer's wrist 23, the device not being provided with a backing plate.

The backing plate 8 serves a number of functions. When the inner magnet member is in certain positions, there is a tendency for it to rotate with respect to the outer magnet member 26. This is due to the fact that like poles repel. Fixing a plate over the inner and outer magnet members prevents such rotation. Furthermore, the placing of a steel plate over the magnet members increases the magnetic field strength experienced by the wearer.

A magnotherapy device according to the invention may be provided with a plurality of straps to provide for secure fitting of the device to a part of a human or animal body.

FIGS. 7a, 7b, 8a, and 8b show the magnetic fields created by different orientations of the inner magnet 1 and the outer magnet 3. The field lines 26 and 27 represent the pattern formed when a layer of iron filings is subjected to the magnetic field created by the different orientations of the inner magnet 1 and the outer magnet 3.

Figure 7A:
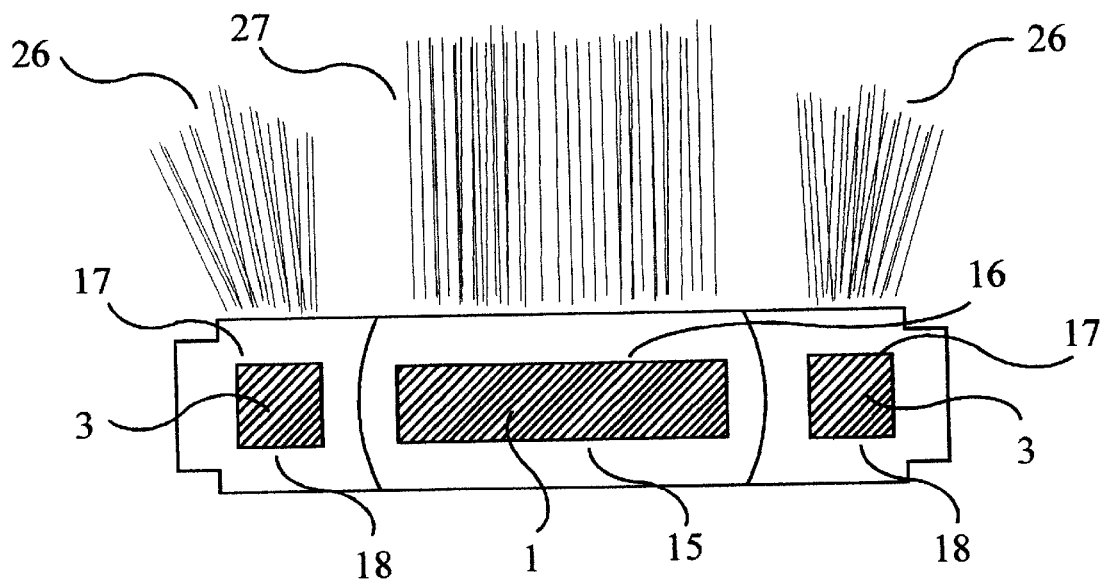
FIG. 7a illustrates a vertical cross-section of the magnetic field produced by the device with the magnets in one orientation.
Figure 8A:
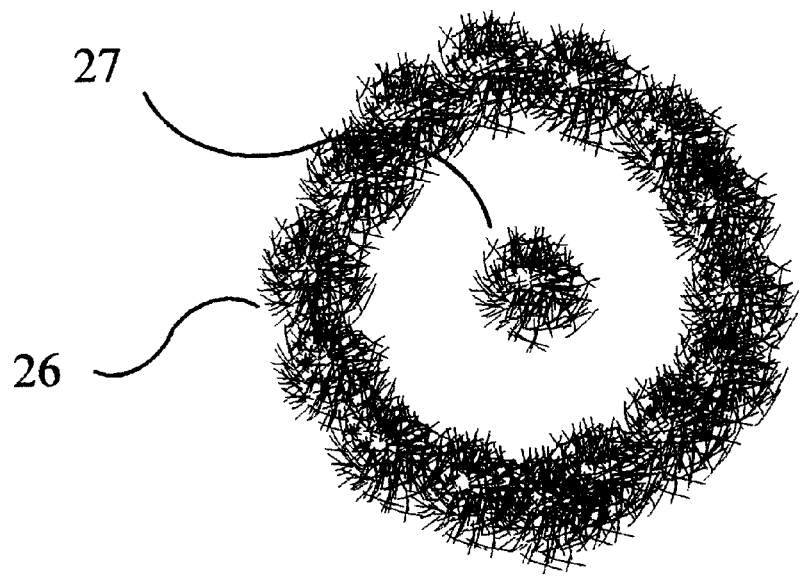

From FIGS. 7a and 8a it can be seen that when both the inner magnet 1 and the outer magnet 3 are oriented in the same direction a strong pencil like magnetic field is generated. The magnetic field is particularly suitable for treating areas of severe pain where muscular discomfort is the main symptom, and problems associated with crystalline deposits in joints.

Figure 7B:
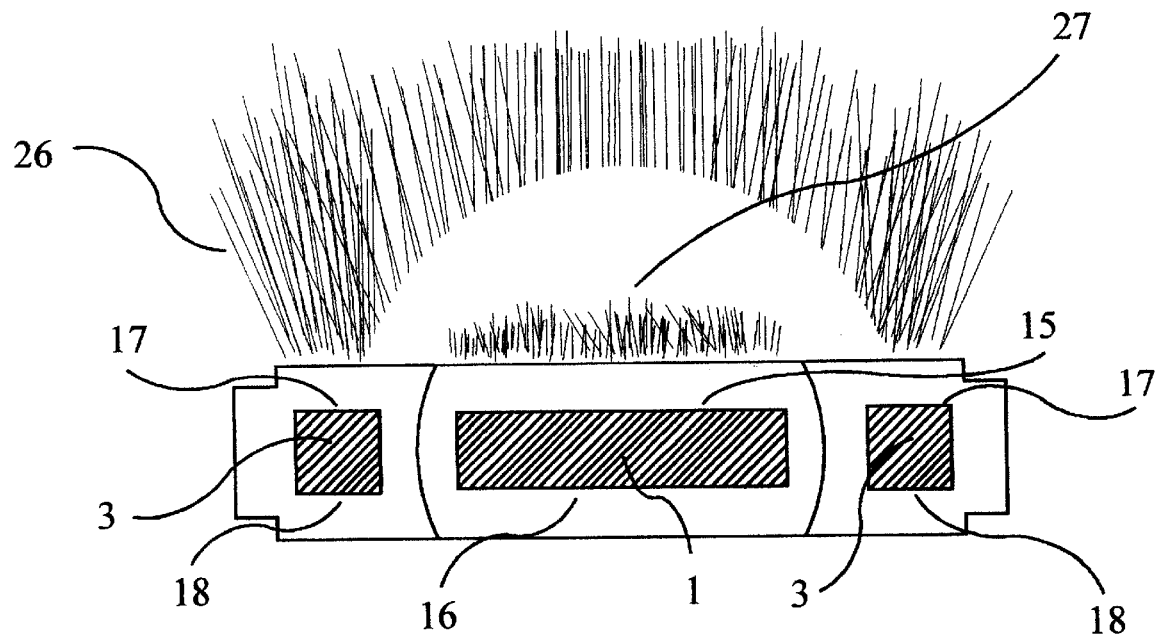
FIG. 7b illustrates a vertical cross-section of the magnetic field produced by the device with the magnets in another orientation.
Figure 8B:
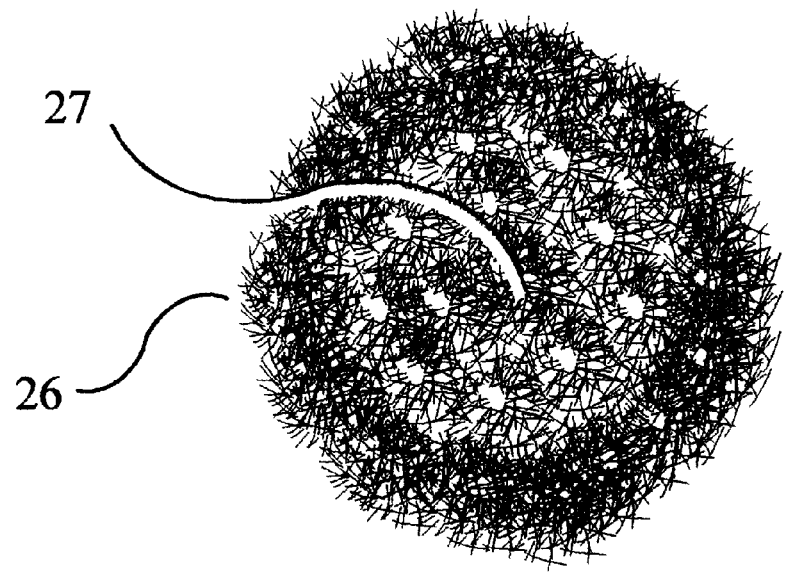
FIG. 8b is a plane view of the magnetic field shown in FIG. 7b.

The arrangement of the magnets 1 and 3 in FIGS. 7b and 8b (i.e. north, south, north) produces a much more diffuse field, which is more suitable for treating conditions such as poor blood supply.

What I claim as my invention is:

1. A magnotherapy device comprising at least two magnet members, mounting means mounting said magnet members, wherein each magnet member has opposing north and south poles, and at least one of the magnet members is mounted by said mounting means so as to be movable relative to another of the said magnet members, thereby enabling the poles of any two adjacent magnet members facing in the same direction to be either opposite or identical.

2. A device according to claim 1, wherein the said at least one of the magnet members mounted so as to be movable relative to another of the said magnet members is rotatably mounted.

3. A device according to claim 1, wherein the said mounting means includes a housing.

4. A device according to claim 3, wherein an outer magnet member is mounted in the housing, and an inner magnet member is mounted within the outer magnet member.

5. A device according to claim 4, wherein the inner magnet member is rotatably mounted within the outer magnet member.

6. A device according to claim 4, wherein the outer magnet member, and/or the inner magnet member comprises a magnet mounted in a casing.

7. A device according to claim 4, wherein the inner magnet member is in the form of a disc.

8. A device according to claim 7, wherein the outer magnet member has a space therein in which the inner magnet is mounted.

9. A device according to claim 8 wherein the space is an aperture.

10. A device according to any preceding claim, wherein the outer magnet member is substantially circular.

11. A device according to claim 4 wherein the magnetic field strength provided by the inner magnet is at least 200 gauss at a distance of 10 mm from the housing.

12. A device according to any preceding claim, further comprising means to maintain the said at least one of the magnet members mounted so as to be movable relative to another of the said magnet members in a fixed position.

13. A device according to claim 12 wherein the said means comprises a plate.

14. A device according to claim 13, wherein the plate is removably mounted to the housing.

15. A device according to any preceding claim, further comprising a strap.

16. A device according to claim 15, wherein the strap is adjustable.

17. A device according to claim 15 and 16, further comprising at least one plug having at one end thereof a means for attachment to a strap, and at the other end thereof means for attachment to the said housing.

18. A device according to claim 17, wherein the means for attachment to the said housing comprises a resiliently mounted member having a protrusion thereon for engagement with an indent in the said housing.

19. A device according to claim 17, wherein the device comprises two of the said plugs.

20. A device according to any preceding claim, wherein at least one of the magnets is a neodymium magnet.

* * * * *